US012797436B2

(12) United States Patent
Lütken et al.

(10) Patent No.: US 12,797,436 B2

(45) Date of Patent: Nov. 17, 2026

(54) COMPOUNDS FOR USE IN THE TREATMENT OF AN ENVELOPED VIRUS INFECTION

(71) Applicant: PHARMA HOLDINGS AS, Tromsø (NO)

(72) Inventors: Christian Lütken, Oslo (NO); Johnny Ivar Ryvoll, Tromsø (NO); Torsteinn Erlingsson, Tromsø (NO)

(73) Assignee: PHARMA HOLDINGS AS (NO)

(*) Notice: Subject to any disclaimer, the term of this patent is extended or adjusted under 35 U.S.C. 154(b) by 471 days.

(21) Appl. No.: 18/546,794

(22) PCT Filed: Mar. 18, 2022

(86) PCT No.: PCT/EP2022/057220

§ 371 (c)(1),
(2) Date: Aug. 17, 2023

(87) PCT Pub. No.: WO2022/195097

PCT Pub. Date: Sep. 22, 2022

(65) Prior Publication Data

US 2024/0156893 A1 May 16, 2024

(30) Foreign Application Priority Data

Mar. 19, 2021 (GB) ..................................... 2103872

(51) Int. Cl.

| | |
|---|---|
| ***A61K 38/06*** | (2006.01) |
| ***A61P 31/16*** | (2006.01) |
| ***C07K 5/09*** | (2006.01) |

(52) U.S. Cl.

CPC .............. *A61K 38/06* (2013.01); *A61P 31/16* (2018.01); *C07K 5/0817* (2013.01)

(58) Field of Classification Search

None

See application file for complete search history.

(56) References Cited

U.S. PATENT DOCUMENTS

| | | | |
|---|---|---|---|
| 8,598,114 | B2 | 12/2013 | Stensen et al. |
| 9,556,223 | B2 | 1/2017 | Stensen et al. |
| 2011/0172145 | A1 | 7/2011 | Stensen et al. |
| 2013/0178466 | A1 | 7/2013 | Bannister et al. |
| 2019/0224362 | A1 | 7/2019 | Kim et al. |
| 2024/0156893 | A1 | 5/2024 | Lütken et al. |

FOREIGN PATENT DOCUMENTS

| | | | |
|---|---|---|---|
| JP | 2011507822 | A | 3/2011 |
| WO | 2009033801 | | 3/2009 |
| WO | 2009081151 | | 7/2009 |
| WO | WO-2009081152 | A2 | 7/2009 |
| WO | WO-2010038041 | A1 | 4/2010 |
| WO | WO-2014191392 | A1 | 12/2014 |
| WO | 2016205798 | | 12/2016 |
| WO | WO-2018138292 | A1 | 8/2018 |
| WO | 2021250283 | | 12/2021 |
| WO | 2021250286 | | 12/2021 |
| WO | WO-2022195097 | A1 | 9/2022 |
| WO | WO-2022200224 | A1 | 9/2022 |
| WO | 2023072485 | | 5/2023 |

OTHER PUBLICATIONS

Wisskirchen et al. "New pharmacological strategies to fight enveloped viruses" Trends in Pharmacological Science 35:470-478. (Year: 2014).*

Nilsson et al. "LTX-109 Is a Novel Agent for Nasal Decolonization of Methicillin-Resistant and -Sensitive *Staphylococcus aureus*" Antimicorbial Agents and Chemotherapy 59:145-151. (Year: 2014).*

Larsen et al. "Antifungal properties of peptidomimetics with an arginine-[B-(2,5,7-tri-tert-butylindol-3-yl)alanine]-arginine motif against *Saccharomyces cerevisiae* and Zygosaccharomyces bailii" FEMS Yeast Research 15:fov011 (Year: 2015).*

Jackman J "Antiviral peptide engineering for targeting membrane-enveloped viruses: Recent progress and future directions" BBA—Biomembranes 1864:183821. (Year: 2022).*

"United Kingdom Application GB2115324.2, Combined Search and Examination Report dated Apr. 6, 2022", (Apr. 6, 2022), 8 pgs.

"International Application No. PCT EP2022 076271, International Search Report and Written Opinion dated Jan. 2, 2023", (Jan. 2, 202), 15 pgs.

Dai, Wenhao, "Design Synthesis and Biological Evaluation of Peptidomimetic Aldehydes as Broad Spectrum Inhibitors against Enterovirus and SARS CoV 2", J Med Chem 2022 65 4 pages, (Apr. 19, 2021), pp. 2794-2808.

Krogsgaard Larsen, Povl, "Textbook of Drug Design and Development", Chapter 14, (Apr. 1, 1996), 2 pages.

CN application 2022800718556 Preliminary Examination mailed Jun. 17, 2024 with English translation, 2 pgs.

"International Application No. PCT/EP2022/057220, International Search and Written Opinion dated Jul. 4, 2022", (Jul. 4, 2022), 9 pgs.

"United Kingdom Application GB2103872.4, Combined Search and Examination Report dated Aug. 9, 2021", (Aug. 9, 2021), 7 pgs.

Allmendinger, Thomas, et al., "Fluoroolefin Dipeptide Isosteres—I.", Tetrahedron Letters, vol. 31, No. 50, pp. 7297-7300 (1990), (1990), 7297-7300.

Chorev, Michael, et al., "A dozen years of retro-inverso peptidomimetics", Chem. Res. 1993, 26, 5, 266-273, (May 1, 1993), 266-273.

Hoffman, Robert V., et al., "The Stereoselective Synthesis of 2-Alkyl.gamma.-Keto Acid and Heterocyclic Ketomethylene Peptide Isostere Core Units Using Chiral Alkylation by 2-Triflyloxy Esters", 1995, 60, 16, 5107-5113, (Aug. 1, 1995), 5107-5113.

(Continued)

*Primary Examiner* — Sudhakar Katakam

*Assistant Examiner* — Zachary J Miknis

(74) *Attorney, Agent, or Firm* — Mueting Raasch Group

(57) ABSTRACT

The present invention provides a compound for use in the treatment of an enveloped virus infection in a subject, wherein said compound is a compound of Formula (I) as defined herein: AA-AA-AA-X-Y-Z (I). The invention further provides a method of treating an enveloped virus infection in a subject, which method comprises administering to a subject in need thereof an effective amount of a compound of Formula (I).

13 Claims, 1 Drawing Sheet

(56) References Cited

OTHER PUBLICATIONS

Lavielle, S., et al., "Importance of the leucine side-chain to the spasmogenic activity and binding of Substance P analogues", International Journal of Peptide and Protein Research, vol. 42, Issue 3, pp. 270-277, (Sep. 1993), 270-277.
Luisi, Grazia, et al., "?(SO2—NH) transition state isosteres of peptides. Synthesis of the glutathione disulfide analogue", Tetrahedron Letters; vol. 34, Issue 14, Apr. 2, 1993, pp. 2391-2392, (Mar. 9, 2001), 2391-2392.
Ostresh, John M., et al., ""Libraries from libraries": Chemical transformation of combinatorial libraries to extend the range and repertoire of chemical diversity", Proc. Natl. Acad. Sci. USA, vol. 91, pp. 11138-11142, (Nov. 1994), 11138-11142.
Reed, L. J., et al., "A Simple Method of Estimating Fifty Per Cent Endpoints", American Journal of Epidemiology, vol. 27, Issue 3, May 1938, pp. 493-497, https://doi.org/10.1093/oxfordjournals.aje.a118408, (May 1, 1938), 493-497.
Saravolatz, Louis D., et al., "In Vitro Activities of LTX-109, a Synthetic Antimicrobial Peptide, against Methicillin-Resistant, Vancomycin-Intermediate, Vancomycin Resistant, Daptomycin-Nonsusceptible, and Linezolid-Nonsusceptible *Staphylococcus aureus*", Antimicrobial Agents and Chemotherapy; vol. 56, No. 8, p. 4478-4482, Aug. 2012, (Aug. 2012), 4478-4482.
Sasaki, Yusuke, et al., "Protection of ? (CH2NH) peptide bond with 2, 4-dimethoxybenzyl group in solid-phase peptide synthesis", Chem. Pharm. Bull. 45 (1), 13-17 (1997), (1997), 13-17.
Schmidt, Ralf, et al., "Structure-activity relationships of dermorphin analogues containing N-substituted amino acids in the 2-position of the peptide sequence", In !. J. Peptide Protein Res. 46, 1995, 47-55, (Jan. 8, 1995), 47-55.
Sherman, Douglas B., et al., "Compatibility of thioamides with reverse turn features: synthesis and conformational analysis of two model cyclic pseudopeptides containing thioamides as backbone modifications", J. Am. Chem. Soc. 1990, 112, 1, 433-441, (Jan. 1, 1990), 433-441.
Spatola, Arno F., "2—Synthesis of Pseudopeptides", Methods in Neurosciences, vol. 13, 1993, pp. 19-42, (1993), 19-42.
"International Application No. PCT/EP2022/057213, International Search Report and Written Opinion dated Jul. 4, 2022", (Jul. 4, 2022), 10 pgs.
"United Kingdom Application GB2104348.4, Combined Search and Examination Report dated Aug. 27, 2021", (Aug. 27, 2021), 6 pgs.
Nilsson, Anna C., et al., "LTX-109 Is a Novel Agent for Nasal Decolonization of Methicillin-Resistant and -Sensitive *Staphylococcus aureus*", Antimicrobial Agents and Chemotherapy, Jan. 2015 vol. 59 No. 1, (Oct. 20, 2014), 145-151.
"EP Application No. 22783501.4-1109 Communication pursuant to Article 943 EPC mailed Oct. 20, 2025", 8 pages.
"International Application No. PCT/EP2022/057213, International Preliminary Report on Patentability dated Oct. 5, 2023", (Oct. 5, 2023), 7 pgs.
"International Application No. PCT/EP2022/057220, International Preliminary Report on Patentability mailed Sep. 28, 2023", (Sep. 28, 2023), 7 pgs.
Bojsen, "The synthetic amphipathic peptidomimetic LTX109 is a potent fungicide that disturbs plasma membrane integrity in a sphingolipid dependent manner" 2013, *PLoS One,* vol. 8, No. 7, 8pgs.
Japan Patent Application No. 2023-557682, filed Mar. 5, 2024; Office Action issued Mar. 3, 2026, English language translation included.
U.S. Appl. No. 18/546,799; Office Action issued Feb. 19, 2026; Examiner: Kristina M. Hellman. 9 pages.
U.S. Appl. No. 18/697,318; Office Action issued Jun. 25, 2026; Examiner: Jeffrey S. Lundgren. 6 pages.
U.S. Appl. No. 18/546,799; Office Action issued Jun. 3, 2026; Examiner: Kristina M. Hellman. 28 pages.
Cilloniz et al., "Epidemiology, pathophysiology, and microbiology of community-acquired pneumonia" Jan. 9, 2018, Ann Res Hosp, vol. 2:1, 11 pgs.
Ruuskanen et al., "Viral Pneumonia" Apr. 9, 2011, Lancet, vol. 377, pp. 1264-1275.
European Patent Application No. 22713679.3, Communication Pursuant to Article 94(3) EPC issued Jul. 23, 2026, 9 pages.
European Patent Application No. 22716905.9, Communication Pursuant to Article 94(3) EPC issued Jul. 23, 2026, 8 pages.

* cited by examiner

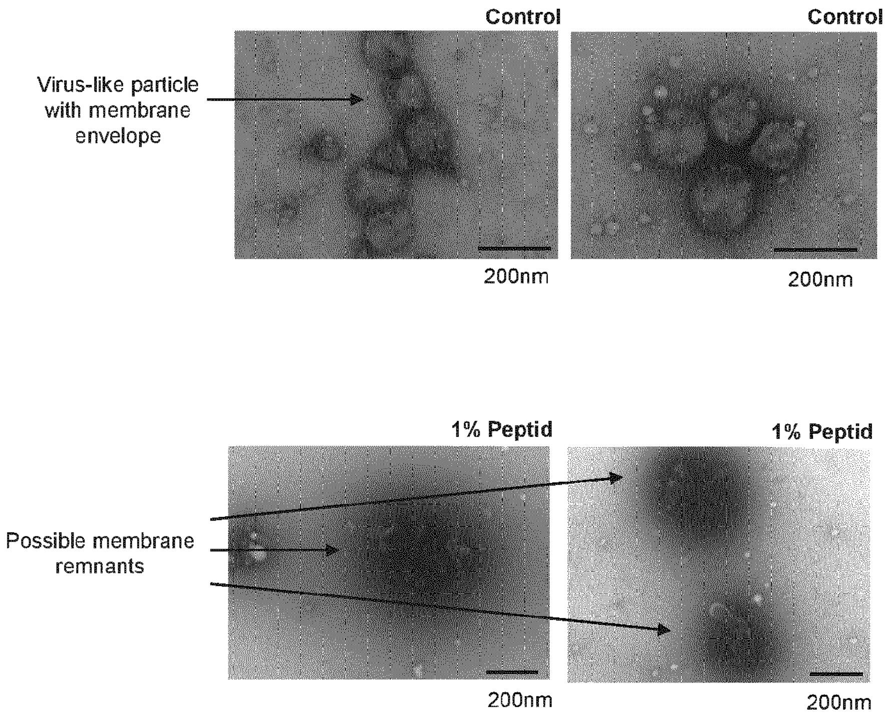
Control
Control
Virus-like particle with membrane envelope
200nm
200nm
1% Peptid
1% Peptid
Possible membrane remnants
200nm
200nm

COMPOUNDS FOR USE IN THE TREATMENT OF AN ENVELOPED VIRUS INFECTION

PRIORITY CLAIM TO RELATED APPLICATIONS

This application is a U.S. national stage filing under 35 U.S.C. § 371 from International Application No. PCT/EP2022/057220, filed on 18 Mar. 2022, and published as WO2022/195097 on 22 Sep. 2022, which claims the benefit under 35 U.S.C. 119 to Great Britain Application No. 2103872.4, filed on 19 Mar. 2021, the benefit of priority of each of which is claimed herein, and which applications and publication are hereby incorporated herein by reference in their entirety.

The invention relates generally to treatment of certain viral infections. More particularly, the invention relates to the use of certain compounds for the treatment of enveloped virus infections.

Viruses are infectious agents that can only replicate within host organisms. Viruses can infect a variety of living organisms, including humans. Virus particles, when independent from their host cells, typically comprise a viral genome (which may be DNA or RNA, single- or double-stranded, linear or circular) contained within a protein shell called a capsid. In some viruses, termed enveloped viruses, the protein shell is enclosed in a membrane called an envelope. Other viruses are non-enveloped.

Viral infections represent a significant healthcare problem. In the past 20 years the world has seen a rise in the number of outbreaks of viral infections. For example, in 2020, the SARS-CoV-2 virus (severe acute respiratory syndrome coronavirus 2), the enveloped virus that causes COVID-19, forced many parts of the world into "lockdown", with severe and long lasting consequences both for the global economy and for global health. It is of great importance to identify new therapeutic and prophylactic treatments against such viruses.

There are many different types of antiviral agent, for example, entry inhibitors, uncoating inhibitors, release (or exit) inhibitors, protease inhibitors, and nucleotide/nucleoside analogues. By way of example, the small molecule Oseltamivir, which is sold under the brand name Tamiflu, is a neuraminidase inhibitor which inhibits the release of influenza A and B viruses (which are enveloped viruses) from host cells. Viral resistance to antiviral agents is a significant problem in global health care. For example in this regard, mutation in a viral protein can render such a mutated virus resistant to treatment with antiviral drugs that act by targeting that viral protein. For example, mutant influenza A viruses that are resistant to Oseltamivir have been reported.

It is clear that alternative, and preferably advantageous, antiviral treatments (particularly viruses which cause disease in humans) would be highly desirable. Such treatments would be useful in treating or preventing infections by viral pathogens (e.g. in humans).

The present inventors have surprisingly found that a class of tripeptide compounds that carry a certain C-terminal modification exhibit excellent antiviral activity against enveloped viruses, including against enveloped viruses that are pathogenic to humans. Such tripeptides are cationic (positively charged) and bulky. One compound in this class is the compound LTX-109. LTX-109 has previously been reported to exhibit antibacterial activity (e.g. Saravolatz et al., *Antimicrobial Agents and Chemotherapy* (2012), Vol. 56(8) pages 4478-4482), but antiviral activity of these molecules has not previously been demonstrated. Given the findings of the present inventors, such compounds clearly represent an important class of agent to be added to the current arsenal of anti-enveloped virus therapies.

Thus, in one aspect, the present invention provides a compound for use in the treatment of an enveloped virus infection in a subject, wherein said compound is a compound of Formula (I)

$$AA—AA—AA—X—Y—Z \quad (I)$$

wherein, in any order, 2 of said AA (amino acid) moieties are cationic amino acids, preferably lysine or arginine but may be histidine or any non-genetically coded or modified amino acid carrying a positive charge at pH 7.0, and 1 of said AA is an amino acid with a large lipophilic R group, the R group having 14-27 non-hydrogen atoms and preferably containing 2 or more, e.g. 2 or 3, cyclic groups which may be fused or connected, these cyclic groups will typically comprise 5 or 6 non-hydrogen atoms, preferably 6 non-hydrogen atoms (in the case of fused rings of course the non-hydrogen atoms may be shared);

X is a N atom, which may be, but preferably is not, substituted by a branched or unbranched $C_1$-$C_{10}$ alkyl or aryl group, e.g. methyl, ethyl or phenyl, and this group may incorporate up to 2 heteroatoms selected from N, O and S;

Y represents a group selected from —$R_a$—$R_b$—, —$R_a$—$R_b$—$R_b$— and —$R_b$—$R_b$—$R_a$— wherein $R_a$ is C, O, S or N, preferably C, and $R_b$ is C; each of $R_a$ and $R_b$ may be substituted by $C_1$-$C_4$ alkyl groups or unsubstituted, preferably Y is —$R_a$—$R_b$— (in which $R_a$ is preferably C) and preferably this group is not substituted, when Y is —$R_a$—$R_b$—$R_b$— or —$R_b$—$R_b$—$R_a$— then preferably one or more of $R_a$ and $R_b$ is substituted; and Z is a group comprising 1 to 3 cyclic groups each of 5 or 6 non-hydrogen atoms (preferably C atoms), 2 or more of the cyclic groups may be fused; one or more of the rings may be substituted and these substitutions may, but will typically not, include polar groups, suitable substituting groups include halogens, preferably bromine or fluorine and $C_1$-$C_4$ alkyl groups; the Z moiety incorporates a maximum of 15 non-hydrogen atoms, preferably 5-12, most preferably it is phenyl;

the bond between Y and Z is a covalent bond between $R_a$ or $R_b$ of Y and a non-hydrogen atom of one of the cyclic groups of Z.

Suitable non-genetically coded amino acids and modified amino acids which can provide a cationic amino acid include analogues of lysine, arginine and histidine such as homolysine, ornithine, diaminobutyric acid, diaminopimelic acid, diaminopropionic acid and homoarginine as well as trimethylysine and trimethylornithine, 4-aminopiperidine-4-carboxylic acid, 4-amino-1-carbamimidoylpiperidine-4-carboxylic acid and 4-guanidinophenylalanine.

The large lipophilic R group of the AA may contain hetero atoms such as O, N or S, typically there is no more than one heteroatom, preferably it is nitrogen. This R group will preferably have no more than 2 polar groups, more preferably none or one, most preferably none.

Compounds for use in accordance with the invention are preferably peptides.

Compounds for use in accordance with the invention are preferably of formula (II)

$$AA_1—AA_2—AA_1—X—Y—Z \qquad (II)$$

wherein:

$AA_1$ is a cationic amino acid, preferably lysine or arginine but may be histidine or any non-genetically coded or modified amino acid carrying a positive charge at pH 7.0;

$AA_2$ is an amino acid with a large lipophilic R group, the R group having 14-27 non-hydrogen atoms and preferably containing 2 or more, e.g. 2 or 3, cyclic groups which may be fused or connected, these cyclic groups will typically comprise 5 or 6 non-hydrogen atoms, preferably 6 non-hydrogen atoms; and X, Y and Z are as defined above.

Further preferred compounds for use in accordance with the invention include compounds of formulae (III) and (IV):

$$AA_2—AA_1—AA_1—X—Y—Z \qquad (III)$$

$$AA_1—AA_1—AA_2—X—Y—Z \qquad (IV)$$

wherein $AA_1$, $AA_2$, X, Y and Z are as defined above. Molecules of formula (II) are more preferred.

From amongst the above compounds certain are particularly preferred. In particular, compounds wherein the amino acid with a large lipophilic R group, conveniently referred to herein as $AA_2$, is tributyl tryptophan (Tbt) or a biphenylalanine derivative such as Phe(4-(2-Naphthyl)), Phe(4-(1-Naphthyl)), Bip (4-n-Bu), Bip (4-Ph) or Bip (4-T-Bu); Phe(4-(2-Naphthyl)) and Tbt being most preferred. In some preferred embodiments, the amino acid with a lipophilic R group is tributyl tryptophan (Tbt).

In some preferred embodiments, Y is $—R_a—R_b—$ and unsubstituted, most preferably $R_a$ and $R_b$ are both carbon (C) atoms. Preferably, Y is $—CH_2—CH_2—$.

In some preferred embodiments, Z is phenyl (Ph).

A further preferred group of compounds are those in which -X-Y-Z together is the group $—NHCH_2CH_2Ph$.

The compounds include all enantiomeric forms, both D and L amino acids and enantiomers resulting from chiral centers within the amino acid R groups and the C-terminal capping group "—X-Y-Z". β and γ amino acids as well as α amino acids are included within the term 'amino acids', as are N-substituted glycines which may all be considered AA units. The compounds for use in accordance with the invention include beta peptides and depsipeptides.

The most preferred compound has the structural formula:

(LTX-109)

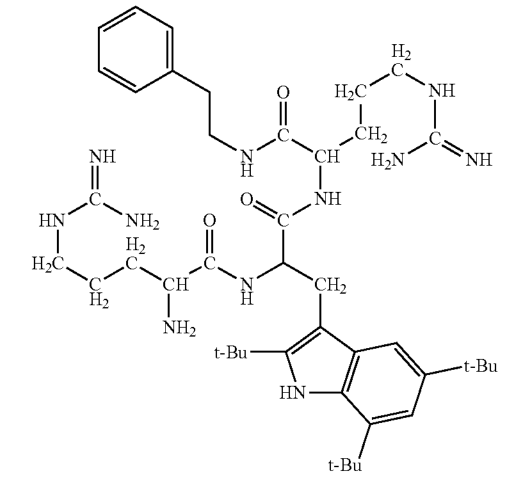

t-Bu represents a tertiary butyl group. This compound with the structural formula above incorporating the amino acid 2,5,7-Tris-tert-butyl-L-tryptophan is the most preferred compound for use in the present invention (and is also referred to herein as LTX-109). Analogues of this compound incorporating other cationic residues in place of Arg, in particular Lys, are also highly preferred. Analogues incorporating alternative C terminal capping groups as defined above are also highly preferred.

Another preferred compound for use in accordance with the present invention is:

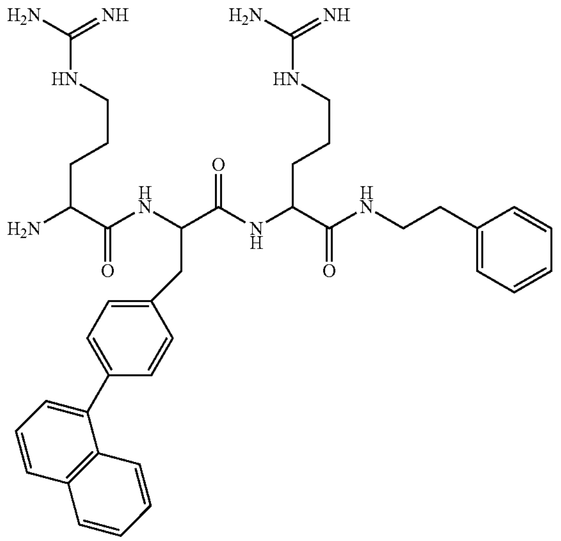 [SMILES: N=C(N)NCCCC(N)C(=O)NC(Cc1ccc(-c2cccc3ccccc23)cc1)C(=O)NC(CCCNC(=N)N)C(=O)NCCc1ccccc1]

This compound (i.e. the compound with the structural formula depicted immediately above) may be referred to as Arg-Phe(4-(1-Naphthyl))-Arg-NH—$CH_2$—$CH_2$-Ph. This compound is a compound of formula (II) in which $AA_1$ is arginine (Arg), $AA_2$ is Phe(4-(1-Naphthyl)), and -X-Y-Z together is the group $—NHCH_2CH_2Ph$.

Another preferred compound for use in accordance with the present invention is:

(LTX-7)

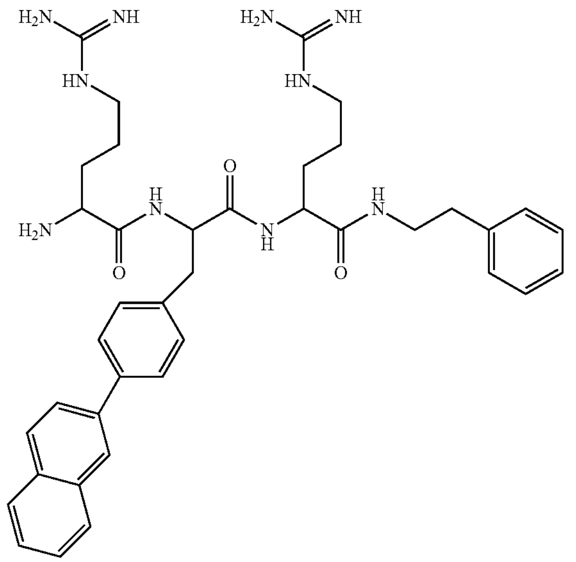

This compound (i.e. the compound with the structural formula depicted immediately above) may be referred to as Arg-Phe(4-(2-Naphthyl))-Arg-NH—$CH_2$—$CH_2$-Ph. This compound is also referred to herein as LTX-7. This compound is a compound of formula (II) in which $AA_1$ is arginine (Arg), $AA_2$ is Phe(4-(2-Naphthyl)), and -X-Y-Z together is the group —$NHCH_2CH_2Ph$.

Another preferred compound for use in accordance with the present invention is:

(LTX-12)

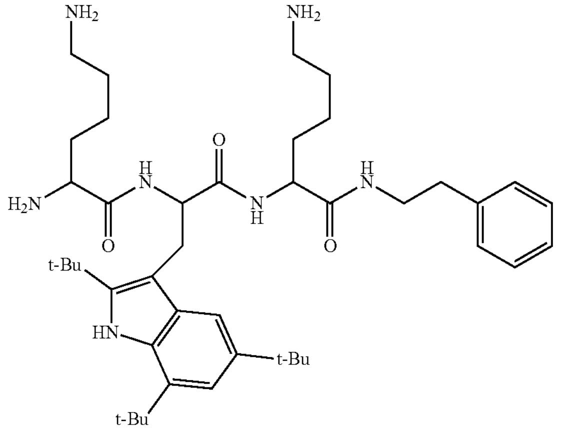

t-Bu represents a tertiary butyl group. This compound (i.e. the compound with the structural formula depicted immediately above) may be referred to as Lys-Tbt-Lys-NH—$CH_2$—$CH_2$-Ph. This compound is also referred to herein as LTX-12. This compound is a compound of formula (II) in which $AA_1$ is lysine (Lys), $AA_2$ is tributyl tryptophan (Tbt, which may also be referred to as 2,5,7-Tris-tert-butyl-L-tryptophan), and -X-Y-Z together is the group —$NHCH_2CH_2Ph$.

In preferred embodiments, the compound for use in accordance with the present invention is selected from the group consisting of LTX-109, LTX-7 and LTX-12. The compound LTX-109 is the most preferred compound for use in accordance with the present invention.

Compounds for use in the present invention are preferably peptides.

The compounds of formulae (I) to (IV) may be peptidomimetics and peptidomimetics of the peptides described and defined herein also represent compounds of use in accordance with the present invention. A peptidomimetic is typically characterised by retaining the polarity, three dimensional size and functionality (bioactivity) of its peptide equivalent but wherein the peptide bonds have been replaced, often by more stable linkages. By 'stable' is meant more resistant to enzymatic degradation by hydrolytic enzymes. Generally, the bond which replaces the amide bond (amide bond surrogate) conserves many of the properties of the amide bond, e.g. conformation, steric bulk, electrostatic character, possibility for hydrogen bonding etc. Chapter 14 of "Drug Design and Development", Krogsgaard, Larsen, Liljefors and Madsen (Eds) 1996, Horwood Acad. Pub provides a general discussion of techniques for the design and synthesis of peptidomimetics. In the present case, where the molecule may be reacting with a membrane rather than the specific active site of an enzyme, some of the problems described of exactly mimicking affinity and efficacy or substrate function are not relevant and a peptidomimetic can be readily prepared based on a given peptide structure or a motif of required functional groups. Suitable amide bond surrogates include the following groups: N-alkylation (Schmidt, R. et al., Int. J. Peptide Protein Res., 1995, 46, 47), retro-inverse amide (Chorev, M and Goodman, M., Acc. Chem. Res, 1993, 26, 266), thioamide (Sherman D. B. and Spatola, A. F. J. Am. Chem. Soc., 1990, 112, 433), thioester, phosphonate, ketomethylene (Hoffman, R. V. and Kim, H. O. J. Org. Chem., 1995, 60, 5107), hydroxymethylene, fluorovinyl (Allmendinger, T. et al., Tetrahydron Lett., 1990, 31, 7297), vinyl, methyleneamino (Sasaki, Y and Abe, J. Chem. Pharm. Bull. 1997 45, 13), methylenethio (Spatola, A. F., Methods Neurosci, 1993, 13, 19), alkane (Lavielle, S. et. al., Int. J. Peptide Protein Res., 1993, 42, 270) and sulfonamido (Luisi, G. et al. Tetrahedron Lett. 1993, 34, 2391).

The peptidomimetic compounds of use in the present invention will typically have 3 identifiable sub-units which are approximately equivalent in size and function to amino acids (AA units). The term 'amino acid' may thus conveniently be used herein to refer to the equivalent sub-unit of a peptidomimetic compound. Moreover, peptidomimetics may have groups equivalent to the R groups of amino acids and discussion herein of suitable R groups and of N and C terminal modifying groups applies, mutatis mutandis, to peptidomimetic compounds.

As is discussed in the text book referenced above, as well as replacement of amide bonds, peptidomimetics may involve the replacement of larger structural moieties with di- or tripeptidomimetic structures and in this case, mimetic moieties involving the peptide bond, such as azole-derived mimetics may be used as dipeptide replacements. Peptidomimetics and thus peptidomimetic backbones wherein the amide bonds have been replaced as discussed above are, however, preferred.

Suitable peptidomimetics include reduced peptides where the amide bond has been reduced to a methylene amine by treatment with a reducing agent e.g. borane or a hydride reagent such as lithium aluminium-hydride. Such a reduction has the added advantage of increasing the overall cationicity of the molecule.

Other peptidomimetics include peptoids formed, for example, by the stepwise synthesis of amide-functionalised polyglycines. Some peptidomimetic backbones will be readily available from their peptide precursors, such as peptides which have been permethylated, suitable methods are described by Ostresh, J. M. et al. in Proc. Natl. Acad. Sci. USA (1994) 91, 11138-11142. Strongly basic conditions will favour N-methylation over O-methylation and result in methylation of some or all of the nitrogen atoms in the peptide bonds and the N-terminal nitrogen.

Preferred peptidomimetic backbones include polyesters, polyamines and derivatives thereof as well as substituted alkanes and alkenes. The peptidomimetics will preferably have N and C termini which may be modified as discussed herein.

The compounds for use in the invention may be synthesised in any convenient way. Generally the reactive groups present (for example amino, thiol and/or carboxyl) will be protected during overall synthesis. The final step in the synthesis will thus be the deprotection of a protected derivative of the invention.

In building up a peptide, one can in principle start either at the C-terminal or the N-terminal although the C-terminal starting procedure is preferred.

Methods of peptide synthesis are well known in the art but for the present invention it may be particularly convenient to carry out the synthesis on a solid phase support, such supports being well known in the art.

A wide choice of protecting groups for amino acids are known and suitable amine protecting groups may include carbobenzoxy (also designated Z) t-butoxycarbonyl (also designated Boc), 4-methoxy-2,3,6-trimethylbenzene sulphonyl (Mtr) and 9-fluorenylmethoxy-carbonyl (also designated Fmoc). It will be appreciated that when the peptide is built up from the C-terminal end, an amine-protecting group will be present on the α-amino group of each new residue added and will need to be removed selectively prior to the next coupling step.

Carboxyl protecting groups which may, for example be employed include readily cleaved ester groups such as benzyl (Bzl), p-nitrobenzyl (ONb), pentachlorophenyl (OPClP), pentafluorophenyl (OPfp) or t-butyl (OtBu) groups as well as the coupling groups on solid supports, for example methyl groups linked to polystyrene.

Thiol protecting groups include p-methoxybenzyl (Mob), trityl (Trt) and acetamidomethyl (Acm).

A wide range of procedures exists for removing amine- and carboxyl-protecting groups. These must, however, be consistent with the synthetic strategy employed. The side chain protecting groups must be stable to the conditions used to remove the temporary α-amino protecting group prior to the next coupling step.

Amine protecting groups such as Boc and carboxyl protecting groups such as tBu may be removed simultaneously by acid treatment, for example with trifluoroacetic acid. Thiol protecting groups such as Trt may be removed selectively using an oxidation agent such as iodine.

Compounds for use in accordance with the present invention (e.g. LTX-109) may be synthesized as described in WO 2009/081152A2.

Compounds (e.g. peptides) for use in accordance with the present invention exhibit activity against enveloped viruses. Put another way, compounds for use in accordance with the present invention exhibit anti-enveloped virus activity.

Compounds of use in the present invention typically exhibit activity against enveloped viruses (anti-enveloped virus activity) in (or as determined by or as assessed by) a suitable in vitro assay, for example an endpoint dilution assay (e.g. a TCID50 assay). The skilled person is familiar with suitable in vitro assays, for example suitable endpoint dilution assays (e.g. TCID50 assays). Preferred TCID50 assays are described in the Example section herein. Compounds of use in the present invention may exhibit activity against enveloped viruses (anti-enveloped virus activity) as determined by (or assessed by) microscopy, e.g. electron microscopy. Compounds of use in the present invention may cause viral envelope disruption (or envelope destabilisation or lysis) as assessed by (or as determined by) any suitable means or assay, for example by microscopy, e.g. electron microscopy. A preferred electron microscopy method is described in Example 1 herein.

Compounds for use in the present invention may exert an anti-enveloped virus effect through a direct membrane (or viral envelope)-affecting mechanism and thus may be considered membrane (or viral envelope) acting antiviral agents. These compounds may thus be considered lytic, destabilising or even perforating the viral envelope. This offers a distinct therapeutic advantage over agents which act on or interact with proteinaceous components of target viruses. Mutations in viral proteins may result in new forms of viral proteins leading to resistance to antiviral agents that act by targeting such viral proteins. However, development of resistance is much less of an issue when the target is a lipid layer (or lipid membrane) (derived from a host cell), as opposed to a particular viral protein target. The envelope-disrupting effect can cause very rapid destruction of enveloped virus particles. In addition to a direct membrane (envelope) disrupting or destabilising activity, the compounds for use in accordance with the invention may have other useful properties which destroy or inhibit the target viruses (e.g. by other mechanisms of action).

As indicated above, the present invention provides compounds as defined elsewhere herein for use in treating enveloped virus infections. Put another way, the present invention provides a compound as defined herein for use in treating an infection in a subject, wherein the causative agent of said infection is an enveloped virus.

"Enveloped viruses" are viruses that are encased in (or enveloped in) a lipid layer (or lipid membrane). The lipid layer may be a lipid bilayer. Thus, enveloped viruses have a capsid (viral capsid) covered by (or encased by or enveloped by or surrounded by) an external membrane, or envelope, which comprises a lipid layer (typically a phospholipid layer), e.g. a lipid bilayer. Viral envelopes may also comprise one or more viral encoded proteins (e.g. glycoproteins). The lipid layer of the viral envelope is derived from (or acquired from) a lipid membrane (e.g. a lipid bilayer) of an infected host cell. Of course, enveloped viruses in accordance with the present invention have an envelope from (or derived from or acquired from) a eukaryotic lipid membrane preferably from a mammalian (e.g. human) lipid membrane. Such a eukaryotic lipid membrane may be the cell membrane or a membrane of a cell organelle (e.g. the endoplasmic reticulum; or the Golgi body (or Golgi apparatus); or the endoplasmic-reticulum-Golgi intermediate compartment (ERGIC) which is sometimes referred to as the vesicular-tubular cluster (VTC)). Viral envelopes are typically acquired at membranes (lipid bilayers) of host cells in a process that may be termed "budding" or "budding off". During the budding process, newly formed virus particles become "enveloped" (or "encased" or "coated") in an outer coat that is made from a lipid membrane of a host cell (host cell of the virus). The lipid layer (or lipid membrane) of the viral envelope can thus be considered as being derived directly from the host cell (derived directly from a membrane of a host cell).

In some embodiments, the enveloped virus is a virus having an envelope (viral envelope) derived from (or acquired from or characteristic of) the cell membrane (i.e. cell membrane of the virus' host cell). The cell membrane may also be referred as the plasma membrane, cytoplasmic membrane or plasmalemma.

In some embodiments, the enveloped virus is a virus having an enveloped (viral envelope) derived from (or acquired from or characteristic of) the membrane of an intracellular organelle (membrane-bound organelle) (i.e. organelle membrane of the virus' host cell). Such membrane-bound organelles include, for example, the endoplasmic reticulum; the Golgi body (or Golgi apparatus); or the endoplasmic-reticulum-Golgi intermediate compartment (ERGIC).

Any enveloped virus infection may be treated in accordance with the present invention. Typically and preferably, the enveloped virus is a virus that infects (or is capable of infecting) a mammal. Mammals include, for example, humans and any livestock, domestic or laboratory animal. Specific examples include mice, rats, pigs, cats, dogs, sheep, rabbits, cows and monkeys. In some embodiments of the present invention the mammal is a human. Thus, typically and preferably, the enveloped virus in accordance with the present invention is mammalian pathogen, preferably a human pathogen.

In some embodiments, the enveloped virus is a causative agent of a respiratory tract infection. The respiratory tract infection may be an infection of the upper and/or lower respiratory tract. In some embodiments, the respiratory tract infection is an infection of the upper respiratory tract.

The enveloped virus may be a DNA virus or a RNA virus. In some embodiments, the enveloped virus is a RNA virus (e.g. a single stranded (ss) RNA enveloped virus).

In some embodiments, the enveloped virus may be a virus of one of the one of the following types: Herpesviruses, Poxviruses, Hepadnaviruses, Asfarviruses, Flaviviruses, Alphaviruses, Togaviruses, Coronaviruses, Orthomyxoviruses, Orthopneumoviruses, Paramyxoviruses, Rhabdoviruses, Bunyaviruse, Filoviruses or Retroviruses.

In some embodiments, the enveloped virus is an Orthopneumovirus (e.g. Respiratory Syncytial Virus, RSV), an Orthomyxovirus (e.g. an Influenza virus such as the Influenza A virus) or a Coronavirus (e.g. the Severe Acute Respiratory Syndrome Coronavirus 2, SARS-CoV-2).

In some embodiments, the enveloped virus is an Orthopneumovirus (e.g. Respiratory Syncytial Virus, RSV).

In some embodiments, the enveloped virus is an Orthomyxovirus (e.g. the Influenza A virus).

In some embodiments, the enveloped virus is a Coronavirus (e.g. the Severe Acute Respiratory Syndrome Coronavirus 2, SARS-CoV-2).

In some embodiments, the enveloped virus is selected from the group consisting of Respiratory Syncytial Virus (RSV), Influenza A virus and Severe Acute Respiratory Syndrome Coronavirus 2 (SARS-CoV-2).

In some embodiments, the enveloped virus is Respiratory Syncytial Virus (RSV). RSV can cause infections of the respiratory tract, e.g. in humans. In some embodiments, the enveloped virus is not RSV.

In some embodiments, the enveloped virus is the Influenza A virus. Influenza A can cause infections of the respiratory tract, e.g. in humans. In some embodiments, the enveloped virus is not the Influenza A virus.

In some embodiments, the enveloped virus is the Severe Acute Respiratory Syndrome Coronavirus 2 (SARS-CoV-2). SARS-CoV-2 can cause infections of the respiratory tract, e.g. in humans. SARS-CoV-2 is the virus that can cause coronavirus disease 2019 (COVID-19). In some embodiments, the enveloped virus is not the SARS-CoV-2 virus.

Alternatively viewed, in one aspect the present invention provides a compound as defined herein for use in treating a disease or condition caused by an enveloped virus infection. Embodiments of other aspects of the invention described herein apply, mutatis mutandis, to this aspect of the invention.

In some embodiments, the disease or condition treated is a respiratory tract infection (e.g. upper and/or lower respiratory tract infection).

In some embodiments, the disease or condition treated is Influenza.

In some embodiments, the disease or condition treated is coronavirus disease 2019 (COVID-19).

Compounds for use in accordance with the invention are typically presented (or administered) in the form of a formulation or composition comprising one or more compounds in accordance with the invention in admixture with a suitable diluent, carrier and/or excipient. Suitable diluents, excipients and carriers are known to the skilled person. Thus, the invention provides a formulation (or composition) comprising a compound as defined herein for use in treating an enveloped virus infection. Typically and preferably of course, the formulation (or composition) is a pharmaceutical formulation (or pharmaceutical composition). Thus, preferably diluents, carriers and/or excipients are pharmaceutically acceptable diluents carriers and/or carriers.

The compositions for use according to the invention may be presented, for example, in a form suitable for oral, nasal, respiratory tract (e.g. upper respiratory tract), parenteral, intravenal, topical or rectal administration. The skilled person is readily able to select an appropriate form for administration, for example based on the type of (or location of the) infection to be treated.

The compounds (or formulations or compositions) for use in accordance with the invention may be administered orally, nasally, parenterally, intravenously, topically or rectally.

The compounds (or formulations or compositions) for use in accordance with the invention may be administered to the respiratory tract, e.g. the upper respiratory tract.

As used herein, the term "pharmaceutical" includes veterinary applications of the invention.

The active compounds defined herein may be presented in the conventional pharmacological forms of administration, such as tablets, coated tablets, solutions, emulsions, liposomes, powders, capsules or sustained release forms.

Conventional pharmaceutical excipients as well as the usual methods of production may be employed for the preparation of these forms.

Tablets may be produced, for example, by mixing the active ingredient or ingredients with known excipients, such as for example with diluents, such as calcium carbonate, calcium phosphate or lactose, disintegrants such as corn starch or alginic acid, binders such as starch or gelatin, lubricants such as magnesium stearate or talcum, and/or agents for obtaining sustained release, such as carboxypolymethylene, carboxymethyl cellulose, cellulose acetate phthalate, or polyvinylacetate.

The tablets may if desired consist of several layers. Coated tablets may be produced by coating cores, obtained in a similar manner to the tablets, with agents commonly used for tablet coatings, for example, polyvinyl pyrrolidone or shellac, gum arabic, talcum, titanium dioxide or sugar. In order to obtain sustained release or to avoid incompatibilities, the core may consist of several layers too. The tablet-coat may also consist of several layers in order to obtain sustained release, in which case the excipients mentioned above for tablets may be used.

Solutions (e.g. injection solutions) may, for example, be produced in the conventional manner, such as by the addition of preservation agents, such as p-hydroxybenzoates, or stabilizers, such as EDTA. The solutions may be filled into vials or ampoules.

Capsules containing one or several active ingredients may be produced, for example, by mixing the active ingredients with inert carriers, such as lactose or sorbitol, and filling the mixture into gelatin capsules.

Suitable suppositories may, for example, be produced by mixing the active ingredient or active ingredient combinations with the conventional carriers envisaged for this purpose, such as natural fats or polyethyleneglycol or derivatives thereof.

Dosages may vary based on parameters such as the age, weight and sex of the subject. Appropriate dosages can be readily established by the skilled person. Appropriate dosage units can readily be prepared.

Treatments in accordance with the present invention may involve co-administration with one or more further active agent that is used in the treatment or prevention of enveloped virus infections (or conditions caused thereby). Speaking generally, the one or more further active agent may be administered to the subject substantially simultaneously with the compound in accordance with the invention; such as from a single pharmaceutical composition or from two pharmaceutical compositions administered closely together. Thus, in some embodiments, pharmaceutical compositions may additionally comprise one or more further active ingredients (e.g. one or more further antiviral compounds). Alternatively, one or more further active agent may be administered to the subject at a time sequential to the administration of a compound in accordance with the invention. "At a time sequential", as used herein, means "staggered", such that the one or more further agent is administered to the subject at a time distinct to the administration of the compound in accordance with the invention. Generally, the two agents would be administered at times effectively spaced apart to allow the two agents to exert their respective therapeutic effects, i.e., they are administered at "biologically effective time intervals". The one or more further active agent may be administered to the subject at a biologically effective time prior to the compound in accordance with the invention, or at a biologically effective time subsequent to the compound in accordance with the invention.

The term "treatment" or "therapy" used herein includes therapeutic and preventative (or prophylactic) therapies. Thus, compounds for use in accordance with the invention may be for therapeutic or prophylactic uses.

Alternatively viewed, the present invention provides a method of treating an enveloped virus infection in a subject (or patient) which method comprises administering to a subject in need thereof a therapeutically or prophylactically effective amount of a compound as defined herein. Embodiments of the invention described herein in relation to other aspects of the invention apply, mutatis mutandis, to this aspect of the invention.

The present invention also provides a method of treating a disease or condition that is caused by (or characterized by) an enveloped virus infection, which method comprises administering to a patient in need thereof a therapeutically or prophylactically effective amount of a compound as defined herein. Embodiments of the invention described herein in relation to other aspects of the invention apply, mutatis mutandis, to this aspect of the invention.

An effective amount (e.g. therapeutically or prophylactically effective amount) will be determined based on the clinical assessment and can be readily monitored. An amount administered should typically be effective to kill or inactivate all or a proportion of the target enveloped viruses or to prevent or reduce their rate of reproduction or otherwise to lessen their harmful effect on the body. Administration may also be prophylactic.

Further alternatively viewed, the present invention provides the use of a compound as defined herein in the manufacture of a medicament for use in the treatment of an enveloped virus infection. Embodiments of the invention described herein in relation to other aspects of the invention apply, mutatis mutandis, to this aspect of the invention.

Further alternatively viewed, the present invention provides the use of a compound as defined herein in the manufacture of a medicament for use in the treatment of a disease or condition that is caused by (or characterized by) an enveloped virus infection. Embodiments of the invention described herein in relation to other aspects of the invention apply, mutatis mutandis, to this aspect of the invention.

Further alternatively viewed, the present invention provides the use of a compound as defined herein for the treatment of an enveloped virus infection. Embodiments of the invention described herein in relation to other aspects of the invention apply, mutatis mutandis, to this aspect of the invention.

Further alternatively viewed, the present invention provides the use of a compound as defined herein for the treatment of a disease or condition that is caused by (or characterized by) an enveloped virus infection. Embodiments of the invention described herein in relation to other aspects of the invention apply, mutatis mutandis, to this aspect of the invention.

In a further aspect is provided a compound of the invention for use in destabilising and/or permeabilising the envelope of an enveloped virus.

The term "subject" or "patient" as used herein includes any mammal, for example humans and any livestock, domestic or laboratory animal. Specific examples include mice, rats, pigs, cats, dogs, sheep, rabbits, cows and monkeys. Preferably, however, the subject or patient is a human subject. Thus, subjects or patients treated in accordance with the present invention will preferably be humans.

In some embodiments, subjects in accordance with the present invention are subjects having an enveloped virus infection. In some embodiments, subjects in accordance with the present invention are subjects suspected of having an enveloped virus infection. In some embodiments, subjects in accordance with the present invention may be subjects at risk of developing (or at risk of contracting) an enveloped virus infection.

In some embodiments, subjects in accordance with the present invention are subjects having a disease or condition caused by an enveloped virus infection. In some embodiments, subjects in accordance with the present invention are subjects suspected of having a disease or condition caused by an enveloped virus infection. In some embodiments, subjects in accordance with the present invention may be subjects at risk of developing (or at risk of contracting) a disease or condition caused by an enveloped virus infection.

The invention also provides kits comprising one or more of the compounds in accordance with the invention for use in the methods and uses described herein. Preferably said kits comprise instructions for use in treating enveloped virus infections as described herein.

As used throughout the entire application, the terms “a” and “an” are used in the sense that they mean “at least one”, “at least a first”, “one or more” or “a plurality” of the referenced components or steps, except in instances wherein an upper limit is thereafter specifically stated.

In addition, where the terms “comprise”, “comprises”, “has” or “having”, or other equivalent terms are used herein, then in some more specific embodiments these terms include the term “consists of” or “consists essentially of”, or other equivalent terms.

The invention will now be further described with reference to the following non-limiting Examples and FIGURE, in which:

FIG. 1: Electron microscopy images of Lenti-virus-like particles following 10 minutes incubation with buffer only (control), or a 1% LTX-109 solution (1% Peptid).

EXAMPLES

Example 1: In Vitro Effect of 1% LTX-109 on Lenti-Virus-Like Particle Envelope The virus used in this Example is a Lenti virus-like particle, expressing a vesicular stomatitis glycoprotein (VSV-G) on the surface. This virus-like particle behaves as a complete enveloped virus, but does not have a genome. The virus samples were loaded onto glow-discharged EM-grids by incubating the grids for 10 minutes with either control virus (in buffer) or virus with 1% LTX-109 final solution. Grids were then dried of with filter paper, and negative stain solution (4% Uranyl acetat in water) was added for 2 min. After removal of staining solution, the grids were dried briefly and then imaged in a JEOL JEM-1230 electron microscope at 80 kV. Images were recorded with a Morada camera and further processed with Adobe Photoshop. The images obtained are shown in FIG. 1.

FIG. 1 clearly shows that Lenti-virus-like particles following the control (buffer only) treatment (incubation) have an intact envelope, whereas the Lenti-virus-like particles following the 1% LTX-109 treatment (incubation) have a disrupted (or dissolved) envelope. Thus, this experiment shows an antiviral membrane-disrupting/destabilising effect of LTX-109 on Lentivirus-like particles.

Example 2: Antiviral Activity of LTX-109 Against Influenza a Virus (IAV)

Aim

The aim of this study was to test the antiviral activity of LTX-109 against IAV (Influenza A virus).

Methods

To test whether 1% LTX-109 (w/v) has antiviral activity against IAV, $1\times10^6$ infectious units of IAV (A/WSN/33; 40 μl) were incubated with four volumes of 1% LTX-109 dissolved in PBS (160 μl) or a PBS (Phosphate-buffered saline) control. The experiment was performed in triplicates.

After 1 hour, the incubation was stopped by adding an excess of cold media, and the formulation was physically separated from the virus through a filter to reduce cytotoxicity on the assay cells. Some cloudiness in the preparation was observed for the 1% formulation, but no precipitation. Infectious virus was quantified through a serial dilution (a series of ten-fold dilutions) on monolayers of MDCK-II cells in microtitre plates (MDCK-II cells are mammalian cells capable of displaying a cytopathic effect (CPE) upon viral infection). The starting solution for the serial dilution (i.e. the neat (or undiluted) solution) was obtained by re-suspending the virus that was separated via the filtration step in 1 ml of media. For each dilution of the virus in the dilution series, eight wells of the microtitre plate were tested (i.e. each dilution of virus was applied to eight separate wells, each well containing a MDCK-II cell monolayer). Appropriate controls were also performed. Five days after infection of the cells, virus titre was quantified by determining the dilution at which half of the cells (half of the wells at a given dilution) displayed virus-induced cytopathic effect (TCID50). The TCID50 (TCID50/ml) assay (Tissue Culture Infectious Dose 50 assay) is a type of endpoint dilution assay that is well known in the art and routinely used to quantitatively measure virus titres. TCID50/ml provides a measure of infectious units of virus/ml. “/ml” refers to/ml of the starting solution (i.e. neat/undiluted solution) mentioned above.

A parallel test where the same procedure was carried out in the absence of virus was included to determine any residual cytotoxic effect of the formulation on the assay cells.

Results

The results of the test for antiviral activity of 1% LTX-109 against Influenza A virus (IAV) are summarized in Table 1 (below).

After incubation with the PBS control for 1 h an average of 5.16E+04 TCID50/ml of IAV was measured.

After 1 h incubation with 1% LTX-109, an average of 1.58E+01 TCID50/ml was measured, which corresponds to a decrease in infectivity of over 3 logs, or 99.9%, as compared to the PBS control.

After filtration, cytotoxicity was observed only up to the first dilution of the 1% formulation, without affecting the validity of the test.

TABLE 1

Average virus titres recovered after incubation with PBS or 1% LTX 109 for 1 h. A decrease of over 3 log of infectivity compared to the PBS control was measured.

| | With Filtration | TCID50/ml ± SEM | Log | Log decrease | Percentage |
|---|---|---|---|---|---|
| PBS 1 h | No cytotoxicity | 5.16E+04 ± 2.11E+04 | 4.62 | | |
| 1% LTX-109 1 h | Up to 10^−1 (i.e. cytotoxicity only up to the $10^{-1}$ dilution) | 1.58E+01 ± 0.00E+00 | 1.20 | 3.42 | 99.969 |

Conclusions

Based on the findings reported here, exposure of IAV to 1% LTX-109 for 1 h in vitro caused over 3 logs decrease in virus infectivity as compared to the PBS control, which corresponds to a 99.9% reduction. These results show that LTX-109 has excellent antiviral activity against Influenza A virus (an enveloped virus).

Example 3: Antiviral Activity of LTX-109 Against Respiratory Syncytial Virus (RSV)

Aim

The aim of this study was to test the antiviral activity of LTX-109 against RSV (Respiratory Syncytial Virus).

Methods

To test whether 1% LTX-109 (w/v) and 0.1% LTX-109 (w/v) have antiviral activity against RSV, $1\times10^5$ infectious units of RSV (40 μl) were incubated with four volumes of 1% LTX-109 or 0.1% LTX-109 dissolved in PBS (160 μl) or a PBS (Phosphate-buffered saline) control. The experiment was performed in triplicates.

After 1 hour, the incubation was stopped by adding an excess of cold media, and the formulation was physically separated from the virus through a filter to reduce cytotoxicity on the assay cells. Some cloudiness in the preparation was observed, particularly for the 1% formulation, but no precipitation. Infectious virus was quantified through a serial dilution (a series of ten-fold dilutions) on monolayers of Hep2 cells in microtitre plates (Hep2 cells are mammalian cells capable of displaying a cytopathic effect (CPE) upon viral infection). The starting solution for the serial dilution (i.e. the neat (or undiluted) solution) was obtained by re-suspending the virus that was separated via the filtration step in 1 ml of media. For each dilution of the virus in the dilution series, eight wells of the microtitre plate were tested (i.e. each dilution of virus was applied to eight separate wells, each well containing a Hep2 cell monolayer). Appropriate controls were also performed. Eight days after infection of the cells, virus titre was quantified by determining the dilution at which half of the cells (half of the wells at a given dilution) displayed virus-induced cytopathic effect (TCID50). The TCID50 (TCID50/ml) assay (Tissue Culture Infectious Dose 50 assay) is a type of endpoint dilution assay that is well known in the art and routinely used to quantitatively measure virus titres. TCID50/ml provides a measure of infectious units of virus/ml. "/ml" refers to/ml of the starting solution (i.e. neat/undiluted solution) mentioned above.

A parallel test where the same procedure was carried out in the absence of virus was included to determine any residual cytotoxic effect of the formulation on the assay cells.

Results

The results of the test for antiviral activity of 1% LTX-109 and 0.1% LTX-109 against Respiratory Syncytial Virus (RSV) are summarized in Table 2 (below).

After incubation with the PBS control for 1 h an average of 3.13E+05 TCID50/ml of RSV 20 was measured.

After 1 h incubation with 1% LTX-109, an average of 1.58E+02 TCID50/ml was measured, which corresponds to a decrease in infectivity of over 3 logs, or 99.9%, as compared to the PBS control.

After 1 h incubation with 0.1% LTX-109, an average of 8.76E+01 TCID50/ml was measured, which corresponds to a decrease in infectivity of over 3 logs, or 99.9%, as compared to the PBS control.

After filtration, cytotoxicity was observed only up to the first dilution of the 1% formulation, without affecting the validity of the test. No cytotoxicity was observed for the 0.1% formulation.

TABLE 2

Average virus titres recovered after incubation with PBS or 1% LTX-109 or 0.1% LTX-109 for 1 h. A decrease of over 3 log of infectivity compared to the PBS control was measured for both of the LTX-109 concentrations tested.

| | With Filtration | TCID50/ml ± SEM | Log | Log decrease | Percentage |
|---|---|---|---|---|---|
| PBS 1 h | No cytotoxicity | 3.13E+05 ± 1.00E+05 | 5.45 | | |
| 1% LTX-109 1 h | Up to 10^−1 (i.e. cytotoxicity only up to the $10^{-1}$ dilution) | 1.58E+02 ± 0.00E+00 | 2.20 | 3.25 | 99.949 |
| 0.1% LTX-109 1 h | No cytotoxicity | 8.76E+01 ± 4.11E+01 | 1.78 | 3.67 | 99.97 |

Conclusions

Based on the findings reported here, exposure of RSV to 1% LTX-109 or 0.1% LTX-109 for 1 h in vitro caused over 3 logs decrease in virus infectivity as compared to the PBS control, which corresponds to a 99.9% reduction. These results show that LTX-109 has excellent antiviral activity against RSV (an enveloped virus).

Example 4: Antiviral Activity of LTX-109 Against the SARS-CoV-2 Virus

Aim

The aim of this study was to test the antiviral activity of LTX-109 against the SARS-CoV-2 virus.

Methods

To test whether 1% LTX-109 (w/v) has antiviral activity against SARS-CoV-2, $5\times10^6$ infectious units of SARS-CoV2 (40 μl) were incubated with four volumes of 1% LTX-109 dissolved in PBS (160 μl) or a PBS (Phosphate-buffered saline) control. The experiment was performed in triplicates.

After 1 hour, the incubation was stopped by adding an excess of cold media, and the formulation was physically separated from the virus through a filter to reduce cytotoxicity on the assay cells. Some cloudiness in the preparation was observed for the 1% formulation, but no precipitation. Infectious virus was quantified through a serial dilution (a series of ten-fold dilutions) on monolayers of Vero cells in microtitre plates (Vero cells are mammalian cells capable of displaying a cytopathic effect (CPE) upon viral infection).

The starting solution for the serial dilution (i.e. the neat (or undiluted) solution) was obtained by re-suspending the virus that was separated via the filtration step in 1 ml of media. For each dilution of the virus in the dilution series, eight wells of the microtitre plate were tested (i.e. each dilution of virus was applied to eight separate wells, each well containing a Vero cell monolayer). Appropriate controls were also performed. Five days after infection of the cells, virus titre was quantified by determining the dilution at which half of the cells (half of the wells at a given dilution) displayed virus-induced cytopathic effect (TCID50). The TCID50 (TCID50/ml) assay (Tissue Culture Infectious Dose 50 assay) is a type of endpoint dilution assay that is well known in the art and routinely used to quantitatively measure virus titres. TCID50/ml provides a measure of infectious units of virus/ml. "/ml" refers to/ml of the starting solution (i.e. neat/undiluted solution) mentioned above.

A parallel test where the same procedure was carried out in the absence of virus was included to determine any residual cytotoxic effect of the formulation on the assay cells.

Results

The results of the test for antiviral activity of 1% LTX-109 against the SARS-CoV-2 virus are summarized in Table 3 (below).

After incubation with the PBS control for 1 h an average of 4.27E+06 TCID50/ml of SARS-CoV-2 was measured.

After 1 h incubation with 1% LTX-109, an average of 1.99E+02 TCID50/ml was measured, corresponding to a decrease in infectivity of over 4 logs, or 99.99%, as compared to the PBS control.

After filtration, cytotoxicity was observed only up to the first dilution of the 1% formulation, without affecting the validity of the test.

TABLE 3

Average virus titres recovered after incubation with PBS or 1% LTX-109 for 1 h. A decrease of over 4 log of infectivity compared to the PBS control was measured.

| | With Filtration | TCID50/ml ± SEM | Log | Log decrease | Percentage |
|---|---|---|---|---|---|
| PBS 1 h | No cytotoxicity | 4.27E+06 ± 7.30E+05 | 6.62 | | |
| 1% LTX 109 1 h | Up to 10^−1 (i.e. cytotoxicity only up to the $10^{-1}$ dilution) | 1.99E+02 ± 4.11E+01 | 2.28 | 4.33 | 99.995 |

Conclusions

Based on the findings reported here, exposure of SARS-CoV-2 to 1% LTX-109 for 1 h in vitro caused over 4 logs decrease in virus infectivity as compared to the PBS control, which corresponds to a 99.99% reduction. These results show that LTX-109 has excellent antiviral activity against SARS-CoV-2 (an enveloped virus).

Example 5: Antiviral Activity of LTX-12 Against the SARS-CoV-2 Virus

Aim

The aim of this study was to test the antiviral activity of LTX-12 against the SARS-CoV-2 virus.

Methods

The SARS-CoV-2 isolate used was from BEI Resources: SARS-CoV-2 isolate England/02/2020 (BEI Resources Catalogue Number (NR52359).

To test whether LTX-12 has antiviral activity against SARS-CoV-2, $7\times10^5$ infectious units of SARS-CoV-2 (40 µl) were incubated with four volumes of 1% LTX-12 (w/v) dissolved in PBS (160 µl) or a PBS (Phosphate-buffered saline) negative control. As a positive control a buffer containing 0.2% Triton in PBS was tested in parallel. Each sample and the PBS control were tested in triplicates.

After 1 hour at room temperature (RT), the incubation was stopped by adding an excess of cold assay media (5 ml), and the formulation was physically separated from the virus through a filter (Sartorius VivaSpin 6, 100000 MWCO, PES (Sartorius, VS0642)) to reduce cytotoxicity on the assay cells. The assay media was M199 medium (Gibco, 41150087) supplemented with 0.4% BSA (Gibco 15260037) and 1×p/s (Gibco 15070063).

Infectious virus was quantified through a serial dilution (a series of ten-fold dilutions, $10^{-1}$ to $10^{-8}$) on a monolayer of Vero cells plated in microtitre plates the day before at 8000 cells/100 µl/well (Vero cells are mammalian cells (African green monkey epithelial cells) capable of displaying a cytopathic effect (CPE) upon viral infection). The starting solution to make the serial dilution (i.e. the neat (or undiluted) solution) was obtained by re-suspending the virus that was separated via the filtration step in 1 ml of assay media, and then making serial dilutions of the starting solution ($10^{-1}$ to $10^{-8}$). For each dilution of the virus in the dilution series ($10^{-1}$ to $10^{-8}$), eight wells of the microtitre plate were tested (i.e. each dilution of virus was applied to eight separate wells, each well containing a Vero cell monolayer). Appropriate controls were also performed. Four days after infection of the cells, virus titre was quantified by determining the dilution at which half of the cells (half of the wells at a given dilution) displayed virus-induced cytopathic effect (TCID50), using the Reed and Muench method (L. J. Reed and H. Muench, *American Journal of Epidemiology*, Volume 27, Issue 3, 1938, Pages 493-497). The TCID50 (TCID50/ml) assay (Tissue Culture Infectious Dose 50 assay) is a type of endpoint dilution assay that is well known in the art and routinely used to quantitatively measure virus titres. TCID50/ml provides a measure of infectious units of virus/ml. "/ml" refers to/ml of the starting solution (i.e. neat/undiluted solution) mentioned above.

A parallel test where the same procedure was carried out in the absence of virus was included to determine any residual cytotoxic effect of LTX-12 on the assay cells.

Results

The results of the test for antiviral activity of LTX-12 against the SARS-CoV-2 virus are summarized in Table 4 (below).

After incubation with the PBS control for 1 h an average of 6.86E+05 TCID50/ml of SARS-CoV-2 was measured.

After 1 h incubation with LTX-12, an average of 1.58E+02 TCID50/ml was measured, corresponding to a decrease in infectivity of over 3 logs, or 99.977%, as compared to the PBS control.

After 1 h incubation with the Triton-based lysis buffer (positive control), 2.80E+01 TCID50/ml was measured, corresponding to a decrease in infectivity of over 4 logs, or 99.996%, as compared to the PBS control.

In the above-mentioned parallel test, no significant cytotoxicity on the Vero cells (assay 35 cells) was observed.

TABLE 4

Average virus titres recovered after incubation with PBS or LTX-12. Virus titre recovered after incubation with Triton-based lysis buffer (positive control) is also shown.

| CONTACT TIME: 1 h | Cytotoxicity | TCID50/ml ± SEM | Log decrease | % Reduction |
|---|---|---|---|---|
| PBS | No cytotoxicity | 6.86E+05 ± 2.03E+05 | | |
| LTX-12 | No cytotoxicity | 1.58E+02 ± 0.00E+00 | 3.58 | 99.977 |
| POSITIVE CONTROL | No cytotoxicity | 2.80E+01 (SEM ND) | 4.34 | 99.996 |

Conclusions

Based on the findings reported here, exposure of SARS-CoV-2 to LTX-12 for 1 hour in vitro caused a decrease of about 3.6 logs in SARS-CoV-2 infectivity as compared to the PBS control, which corresponds to at least 99.9% reduction. These results show that LTX-12 has excellent antiviral activity against SARS-CoV-2 (an enveloped virus).

Triton as a positive control provides a benchmark and confirms the suitability of the assay. Enveloped viruses are known to be susceptible to Triton and while the impact of Triton (positive control) slightly exceeds that of LTX-12, the test peptide (LTX-12) still performs well in comparison.

The cytotoxicity test shows that any residual peptide which may be associated with the virus after the filtration step is not responsible for the activity seen in the TCID50 assay.

Example 6: Antiviral Activity of LTX-7 Against Influenza a Virus

Aim

The aim of this study was to test the antiviral activity of LTX-7 against Influenza A.

Methods

The Influenza A strain used was strain A/WSN/33 (H1N1).

To test whether LTX-7 has antiviral activity against Influenza A, $5\times10^5$ infectious units of Influenza A (40 µl) were incubated with four volumes of 1% LTX-7 (w/v) dissolved in PBS or a PBS (Phosphate-buffered saline) negative control. As a positive control, a buffer containing 0.2% Triton X-100 in PBS was tested in parallel. Each sample and the PBS control were tested in triplicates.

After 1 hour at room temperature (RT), the incubation was stopped by adding an excess of cold assay media (5 ml), and the formulation was physically separated from the virus through a filter (Sartorius VivaSpin 6, 100,000 MWCO, PES (Sartorius, VS0642)) to reduce cytotoxicity on the assay cells. The assay media was DMEM (Gibco 61965-026) supplemented with 0.1% FBS (Gibco 10500-064), 20 mM Hepes (Gibco 15630-056), 0.3% BSA Fraction V (Gibco 15260037) and 1×p/s (Gibco 15070063).

Infectious virus was quantified through a serial dilution (a series of ten-fold dilutions, $10^0$ to $10^{-7}$) on a monolayer of MDCK-II cells plated in microtitre plates the day before at 9,000 cells/100 µl/well (MDCK-II cells are mammalian cells (Madin-Darby canine kidney cells) capable of displaying a cytopathic effect (CPE) upon viral infection). The starting solution for the serial dilution (i.e. the neat (or undiluted) solution or $10^0$ solution) was obtained by re-suspending the virus that was separated via the filtration step in 1 ml of assay media. For each dilution of the virus in the dilution series ($10^0$ to $10^{-7}$), eight wells of the microtitre plate were tested (i.e. each dilution of virus was applied to eight separate wells, each well containing a MDCK-II cell monolayer). Appropriate controls were also performed. Four days after infection of the cells, virus titre was quantified by determining the dilution at which half of the cells (half of the wells at a given dilution) displayed virus-induced cytopathic effect (TCID50), using the Reed and Muench method (L. J. Reed and H. Muench, *American Journal of Epidemiology*, Volume 27, Issue 3, 1938, Pages 493-497). The TCID50 (TCID50/ml) assay (Tissue Culture Infectious Dose 50 assay) is a type of endpoint dilution assay that is well known in the art and routinely used to quantitatively measure virus titres. TCID50/ml provides a measure of infectious units of virus/ml. "/ml" refers to/ml of the starting solution (i.e. neat/undiluted solution) mentioned above.

A parallel test where the same procedure was carried out in the absence of virus was included to determine any residual cytotoxic effect of LTX-7 on the assay cells.

Results

The results of the test for antiviral activity of LTX-7 against Influenza A virus (IAV) are summarized in Table 5 (below).

After incubation with the PBS control for 1 h an average of 1.33E+06 TCID50/ml of Influenza A was measured.

After 1 h incubation with LTX-7, an average of 1.58E+01 TCID50/ml was measured, which corresponds to a decrease in infectivity of over 4 logs, or over 99.99%, as compared to the PBS control.

After 1 h incubation with the Triton X100 lysis buffer (positive control), 1.58E+01 TCID50/ml was measured, corresponding to a decrease in infectivity of over 4 logs, or over 99.99%, as compared to the PBS control.

After filtration, cytotoxicity on the MDCK-II cells was observed (only) with the neat application of the LTX-7 formulation, Triton X-100 (positive control) and PBS (without virus), but without affecting the validity of the test.

TABLE 5

Average virus titres recovered after incubation with PBS or LTX-7. Virus titre recovered after incubation with Triton X-100 lysis buffer (positive control) is also shown.

| CONTACT TIME: 1 h | Cytotoxicity | TCID50/ml ± SEM | Log decrease | % Reduction | Rounded % |
|---|---|---|---|---|---|
| PBS | neat | 1.33E+06 ± 7.64E+05 | | | |
| LTX-7 | neat | 1.58E+01 ± 0.00E+00 | 4.75 | 99.9988 | 99.99% |
| POSITIVE CONTROL | neat | 1.58E+01 (SEM ND) | 4.75 | 99.9988 | 99.99% |

Conclusions

Based on the findings reported here, exposure of Influenza A to LTX-7 for 1 hour in vitro caused a decrease of 4.75-logs in Influenza A infectivity, as compared to the PBS control. This corresponds to at least 99.99% reduction. These results show that LTX-7 has excellent antiviral activity against Influenza A (an enveloped virus).

Triton X-100 as a positive control provides a benchmark and confirms the suitability of the assay. Enveloped viruses are known to be susceptible to Triton X-100. LTX-7 performs as well as the positive control in this study.

The cytotoxicity test shows that direct application of LTX-7 to the MDCK-II cells is only cytotoxic before any serial dilutions are performed (i.e. with the neat formulation). Thus any residual peptide which may be associated with the virus after the filtration step is not responsible for the activity seen in the TCID50 assay.

The invention claimed is:

1. A method for the treatment of a Coronavirus, Orthopneumovirus, or Orthomyxovirus infection in a subject in need thereof, wherein said method comprises administering to said subject an effective amount of a compound of Formula:

(a)

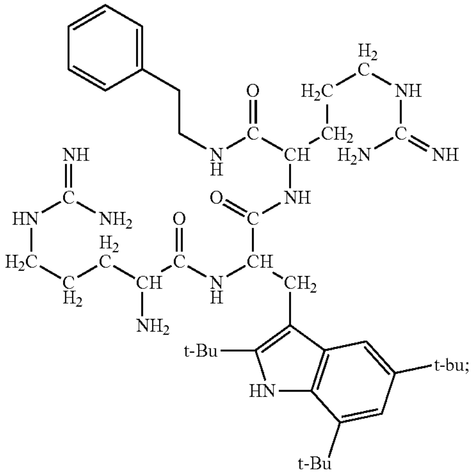 [SMILES: CC(C)(C)c1cc(C(C)(C)C)c2[nH]c(C(C)(C)C)c(CC(NC(=O)C(N)CCCNC(=N)N)C(=O)NC(CCCNC(=N)N)C(=O)NCCc3ccccc3)c2c1]

-continued (b)

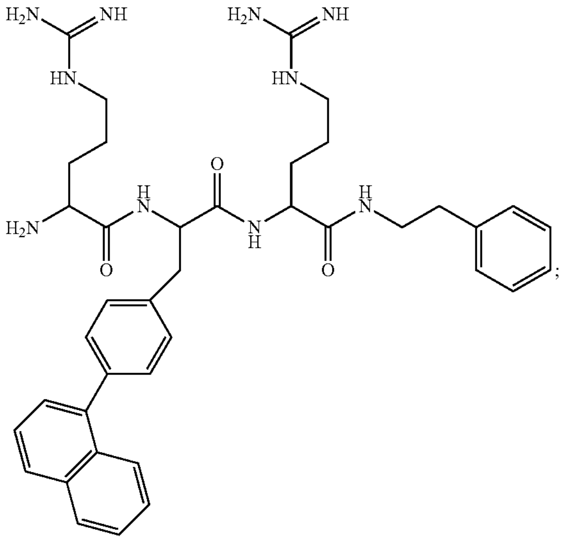

(c)

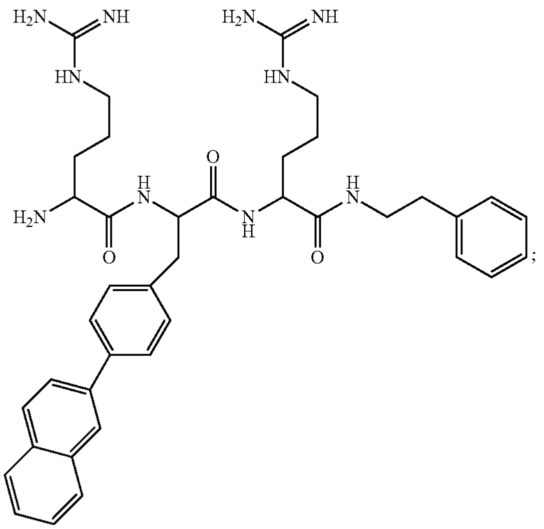

or

-continued (d)

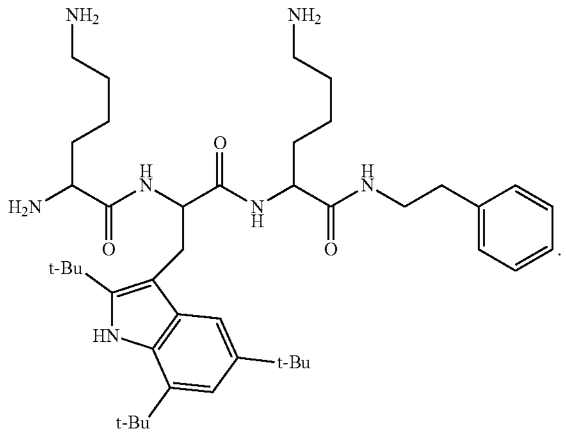

2. The method according to claim 1, wherein said Coronavirus, Orthopneumovirus, or Orthomyxovirus infection is a respiratory tract infection.

3. The method according to claim 1, wherein said Coronavirus is SARS-COV-2.

4. The method according to claim 1, wherein said subject is a human subject.

5. The method according to claim 1, wherein said compound is comprised in a pharmaceutical formulation further comprising a diluent, carrier and/or excipient.

6. The method according to claim 1, wherein said treatment is a therapeutic treatment.

7. The method according to claim 1, wherein said treatment is a prophylactic treatment.

8. The method according to claim 1, wherein said Orthopneumovirus is Respiratory Syncytial Virus (RSV).

9. The method according to claim 1, wherein said Orthomyxovirus is Influenza A virus.

10. The method according to claim 1, wherein said compound is that of Formula (a):

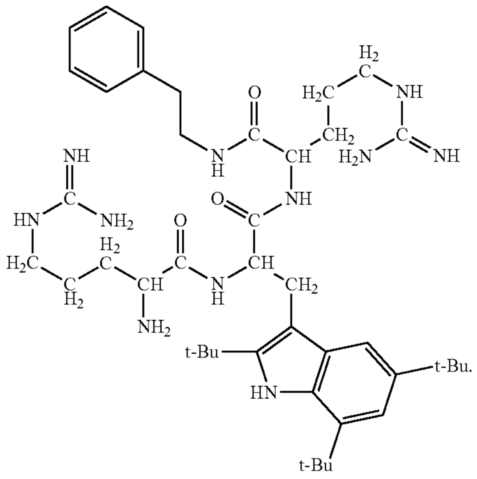 [SMILES: CC(C)(C)c1cc(C(C)(C)C)c2[nH]c(C(C)(C)C)c(CC(NC(=O)C(N)CCCNC(=N)N)C(=O)NC(CCCNC(=N)N)C(=O)NCCc3ccccc3)c2c1]

11. The method according to claim 3, wherein said compound is that of Formula (a):

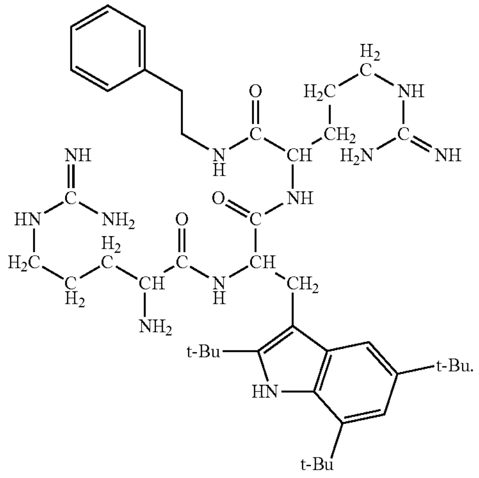 [SMILES: CC(C)(C)c1cc(C(C)(C)C)c2[nH]c(C(C)(C)C)c(CC(NC(=O)C(N)CCCNC(=N)N)C(=O)NC(CCCNC(=N)N)C(=O)NCCc3ccccc3)c2c1]

12. The method according to claim 8, wherein said compound is that of Formula (a):

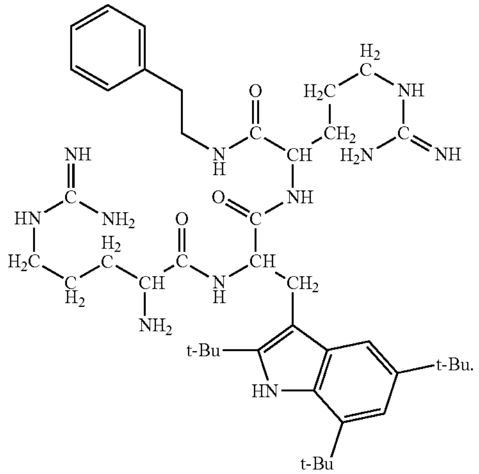 [SMILES: CC(C)(C)c1cc(C(C)(C)C)c2[nH]c(C(C)(C)C)c(CC(NC(=O)C(N)CCCNC(=N)N)C(=O)NC(CCCNC(=N)N)C(=O)NCCc3ccccc3)c2c1]

13. The method according to claim 9, wherein said compound is that of Formula (a):

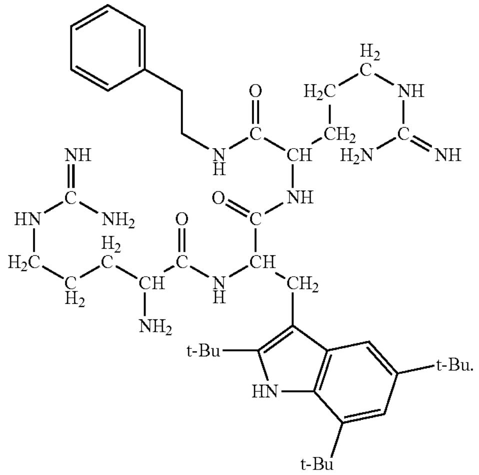

* * * * *